United States Patent [19]

Suekane et al.

[11] 3,935,070
[45] Jan. 27, 1976

[54] PRODUCTION OF SWEET SYRUP FROM DEXTROSE MOTHER LIQUOR

[75] Inventors: Mikio Suekane, Saitamaken; Shiro Hasegawa, Tokyo; Masaki Tamura, Machida; Yoshiyuki Ishikawa, Kunitachi, all of Japan

[73] Assignee: CPC International Inc., Englewood Cliffs, N.J.

[22] Filed: May 22, 1975

[21] Appl. No.: 579,992

Related U.S. Application Data

[63] Continuation of Ser. No. 303,751, Nov. 6, 1972, abandoned.

[52] U.S. Cl. ............... 195/31 F; 195/11; 195/31 R
[51] Int. Cl.² ......................................... C12D 13/02
[58] Field of Search ............ 195/31 R, 31 F, 11, 7, 195/4

[56] References Cited

UNITED STATES PATENTS

| 3,616,221 | 10/1971 | Takasaki et al. | 195/31 F |
| 3,819,484 | 6/1974 | Okada et al. | 195/31 R |

FOREIGN PATENTS OR APPLICATIONS

| 4,540,253 | 12/1970 | Japan | 195/31 F |
| 4,011,897 | 6/1965 | Japan | 195/31 F |

OTHER PUBLICATIONS

Whistler et al., *Starch Chemistry and Technology*, Vol. 1, Academic Press, N.Y. and London, pp. 164, 167–171.

Maher, *Die Starke*, No. 7, pp. 228–233, (1968).

*Primary Examiner*—A. Louis Monacell
*Assistant Examiner*—Thomas G. Wiseman
*Attorney, Agent, or Firm*—Albert P. Halluin, Esq.

[57] ABSTRACT

A process for converting a dextrose mother liquor to a sweet product, comprising subjecting a dextrose mother liquor to isomerization, preferably by the action of an enzyme preparation having dextrose isomerizing activity, to isomerize a substantial part of the dextrose content to levulose, and then subjecting the isomerized liquor to the action of an enzyme preparation having isomaltose activity.

17 Claims, No Drawings

PRODUCTION OF SWEET SYRUP FROM DEXTROSE MOTHER LIQUOR

This is a continuation, of copending application Ser. No. 303,751 filed Nov. 6, 1972, now abandoned.

FIELD OF THE INVENTION

This invention relates to the production of sweet syrups. More particularly, the invention relates to a novel enzymatic process for the production of sweet syrups.

BACKGROUND

As is pointed out in U.S. Pat. No. 3,042,584, granted July 3, 1962, to Earl R. Kooi, Clarence F. Harjes, and John S. Gilkison, amylase preparations of microbiological origin demonstrate three major types of enzyme activity concerned with the hydrolysis of alpha-1, 4-linked glucose polymers, such as starch and starch hydrolysates. These three types of activity may be classified as alpha-amylase activity, glucamylase activity, and transglucosidase activity.

For the enzymatic conversion of starch or thinned starch to produce a high D. E. hydrolysate, the transglucosidase activity is undesirable, since it acts particularly on maltose, to form unfermentable and undesirable dextrose polymers that contain alpha-1, 6-glucosidic linkages.

In commercial operations for the production of high D. E. hydrolysates, the amylase preparations that are used may be treated with clay, to remove the transglucosidase activity. The clay, with the absorbed transglucosidase activity, is easily separated from the amylase enzyme preparation, by filtration or other separation means. The separated clay is considered to be a waste product, and is ordinarily discarded.

OBJECTS OF THE INVENTION

One object of the invention is to provide a novel process for making use of the present waste product, that is, clay that has absorbed transglucosidase activity.

A related object of the invention is to provide a novel process for the production of sweet syrups, that takes advantage of the transglucosidase activity that is currently discarded.

Another related object of the invention is to provide a novel process of the character described, that can be used for upgrading "greens", i.e., mother liquors from which crystalline dextrose has been recovered, but which contain additional, residual dextrose value that cannot now be economically recovered.

Other objects of the invention will be apparent hereinafter from the specification and from the recitals of the appended claims.

DEFINITIONS

Because of the many terms that are in common use in the art, a few definitions are made to simplify the present application and permit it to be more concise.

D. E. The term "D. E." is an abbreviation for "dextrose equivalent", and these terms are used interchangeably to refer to the reducing sugar content of a material calculated as dextrose and expressed as percent of total solids.

Starch hydrolyzate. The term "starch hydrolyzate" is used in a general way to refer to a syrup or dry product that is made by the hydrolysis of starch. Such a product may be made by acid or enzymatic hydrolysis, or by a combination of acid and enzymatic hydrolysis. A preferred type of starch hydrolyzate for use as the supply material for the process of the present invention is the hydrol that is obtained by recovering crystalline dextrose from a starch conversion product obtained by acid or enzyme thinning of starch to a D. E. of 10 or less, followed by enzymatic saccharification to a D. E. above 95, and preferably above 97.5, and crystallization of the dextrose, to leave a mother liquor (hydrol or greens).

Glucose and dextrose. Medium D. E. starch hydrolyzates are commonly referred to in the art as "glucose", whether the starch hydrolyzate is in the form of a syrup or in the form of solids. The term "dextrose" is commonly reserved for the refined crystalline monosaccharide that is recovered from a high D. E. starch hydrolyzate, or for D-glucose as a constituent of starch hydrolyzates. As used hereafter, the term "dextrose" will be used to embrace this monosaccharide in any form, in solution or dry, as a constituent of a starch hydrolyzate syrup, syrup solids, or in refined crystalline form.

Fructose and levulose. The terms "fructose" and "levulose" are generally employed interchangeably in the art to refer to the isomer of dextrose that is sweeter than dextrose. This isomer is found in honey and in invert sugar, along with dextrose, and it is valuable because of its sweetness. The term "levulose" will be used to refer to this monosaccharide.

The isomerase enzyme. The enzyme that isomerizes dextrose to levulose has been referred to in the art by several names. It is referred to in the Marshall U.S. Pat. No. 2,950,228, as xylose isomerase, because it isomerizes xylose to xylulose. This activity is in addition to its ability to isomerize dextrose to levulose. It has also been referred to in the art as dextrose isomerase and glucose isomerase. The term "xylose isomerase" will be used herein.

Enzyme preparation. The term "enzyme preparation" is used to refer to any composition of matter that exhibits the desired xylose isomerase enzymatic activity. The term is used to refer, for example, to live whole cells, dried cells, cell extracts, and refined and concentrated preparations derived from the cells. Enzyme preparations may be either in dry or liquid form.

Isomaltase activity. This term refers to the enzyme activity whose substrate is isomaltose. Transglucosidase enzyme preparations exhibit this activity, along with other activities. Isomaltase enzyme preparations, particularly those from *Aspergillus niger*, convert maltose and isomaltose and other oligosaccharides to dextrose.

Units. In this application, all parts and percentages are by weight, and on an as is basis, unless expressly stated to be otherwise.

Isomerase Unit. One isomerase unit is defined as the amount of enzyme activity that is required to produce one millimicromole of levulose per minute under the isomerization conditions described hereafter under the heading, "Assay of Isomerase Activity."

Isomaltase unit. One isomaltase, or transglucosidase unit, is defined as the amount of enzyme activity that is required to produce one millimicromole of glucose per minute under the reconversion conditions described hereafter under the heading, "Assay of Isomaltose Activity."

ASSAY OF GLUCOSE ISOMERASE ACTIVITY

The assay procedure involves making a spectrophotometric determination of the ketose produced from a glucose solution under a standardized set of conditions.

The assay mixture, in a final volume of 1 ml, containing:

TABLE 1

Stock Solution for Assay

Component 100 micromoles of glucose
10 micromoles of $MgSO_4$
1 micromole of $CoCl_2$
50 micromoles of Tris-HCl buffer (pH 7.5)
Approximately 500 units of the enzyme was incubated at 60°C for 10 minutes. The reaction was terminated by adding 4 ml. of 0.5 N $HClO_4$. Levulose/-formed was determined by the cysteine-carbazol method of Disch and Borenfreund (J. Biol. Chem., 192, 583 (1951)). Intensity of color developed at 60°C for 10 minutes was read at 560 m$\mu$.

For the purpose of this assay, one glucose isomerase unit is defined as the amount of enzyme activity that is required to produce one millimicromole of levulose per minute under these isomerization conditions.

ASSAY OF TRANSGLUCOSIDASE OR ISOMALTASE ACTIVITY

The assay procedure involves making a determination of the glucose produced from an isomaltase solution under a standard set of conditions.

The reaction mixture consists of, in final mole concentration, 0.01 M isomaltose, 0.05 M acetate buffer, pH 4.5, and 0.25 ml. of enzyme solution, thus totaling 0.5 ml. volume. After incubation for 10 minutes at 37°C, the reaction was terminated by heating at 100°C for 5 minutes. The amount of glucose produced was determined by the glucose oxidase method according to Loyd and Whelan (Anal. Biochem. 30, 467 (1969)). For the purposes of this assay, one isomerase unit is defined as the amount of enzyme activity that is required to produce one millimicromole of glucose per minute under these reconversion conditions.

BRIEF SUMMARY OF THE INVENTION SUMMARY

We have now discovered that it is possible to treat a solution that contains isomaltose, maltose, other oligosaccharides, and dextrose in a certain way, to increase its value. The treatment steps are first, to isomerize a substantial part of the dextrose to levulose, preferably by enzymatic isomerization, and then to subject the resultant solution to the action of an enzyme preparation having isomaltase activity or transglucosidase activity. The initial solution preferably is at a concentration not exceeding about 50% dry substance (d. s.).

The process of the invention, in the first step, converts the dextrose to levulose. This decreases the dextrose concentration in the solution. The second step, reconversion, converts most of the isomaltose, maltose, and other oligosaccharides, to dextrose, thereby completing the conversion of most of the original, less valuable polysaccharides to the more valuable monosaccharides.

The end product is a solution of dextrose, levulose and a minor amount of oligosaccharides. It can advantageously be utilized in the production of food, soft drinks and candy, and for several applications in baking, either as a syrup or in dried form.

One important advantage of the process is that it offers an attractive way to utilize greens to make the greens useful for economically valuable applications. Another important advantage is that a high recovery of monosaccharide values is achieved because of the sequence of the steps, which takes advantage of the dextrose-isomaltose-maltose equilibrium in solution, to obtain the high monosaccharide values in the final product.

Greens are a good raw material, for the process of the invention, because they are high in maltose and isomaltose, and also contain dextrose.

DETAILED DESCRIPTION OF THE INVENTION

The invention will now be further described by means of a specific demonstration in the following example.

EXAMPLE 1

Isomerization and Reconversion of Greens; Effect of Dry Solids Content

A deionized greens solution was adjusted to a 50% concentration of dry solids. It was then subjected to enzymatic isomerization. The enzyme dosage was 400 units per gram of solids, d.s., in the greens. The isomerization was conducted at pH 6.5, at 70°C, for 48 hours.

The isomerizate was separated into three portions, and the concentrations were adjusted to 10%, 30%, and 50% d.s., respectively.

These isomerizates were then subjected to the action of transglucosidase, from a clay that had been employed to absorb transglucosidase from amylase. The enzyme dosage was at the rate of 25,000 units of enzyme per gram of dry substance, and the conditions were pH 4.5 at 60°C, for 2 days.

The data are summarized below.

Table 2

| Results of the Isomerization and Reconversion of Greens | | |
|---|---|---|
| Supply Liquor: Greens, % solids, d.b. | End Product Dextrose, % of solids, d.b. | End Product ketose % of solids, d.b. |
| 10 | 70 | 27 |
| 30 | 61 | 27 |
| 50 | 48 | 27 |

The advantages of the invention can be demonstrated by considering what happened to the hydrol (greens) treated by the present process, in the foregoing example.

Greens at 10% d.s., subjected to successive enzymatic isomerization and transglucosidase treatment, produced a syrup containing 70% dextrose, 27% levulose, and a very minor amount of polysaccharides, based on 100 parts d.s. This is a much more valuable syrup product than the original greens. Moreover, it is a superior product to the syrup that would be obtained by treating the greens with transglucosidase above, since such a treatment would produce a syrup containing 90% dextrose, based on 100 parts d.s., with the balance being polysaccharides. This contrasts with the 97% of monosaccharides in the syrup, based on dry substance, obtained by the process of the invention.

Similarly, the 30% d.s. greens, treated in accordance with the invention, produced a syrup containing 88% of monosaccharides based on total solids, the balance being polysaccharides, whereas a treatment with transglucosidase above would produce a product at 82% monosaccharide (dextrose), because of the maltose-isomaltose-dextrose equilibrium factor.

The contrast at 50% solids d.s. is not so great. The process of the invention produces a syrup product containing 75% monosaccharides based on total solids; a treatment with transglucosidase alone would produce a 74% monosaccharide product, d.s.

Accordingly, the advantages of the invention can best be realized when the total solids in the starting material is about 50% or less, d.s. Even so, by a slight modification in processing, the advantages of the invention can be realized. This modification involves a preliminary treatment of the greens with transglucosidase. Thus, greens at 50% solids d.s. can be subjected to the action of transglucosidase to produce a modified greens at 57% dextrose based on total solids; this is the approximate maltose-isomaltose-dextrose equilibrium value. Upon enzymatic isomerization, this is converted to a syrup containing about 44% dextrose, and 30% levulose, for a total monosaccharide content of 74%, based on total solids. Upon further treatment with transglucosidase, the polysaccharides are further converted to produce a final product containing 52% dextrose and 30% levulose, based on total solids, for a total monosaccharide content of 82% based on total solids. In this final product, the dextrose is at equilibrium, substantially, with the maltose content, and the polysaccharide content is 18% based on total solids. Thus, the process of the invention can be used to convert greens at about 50% solids to a syrup product containing predominantly monosaccharides, without diluting the greens.

EXAMPLE 2

Treatment of Second Greens from An Enzyme-Enzyme Hydrolysate

To demonstrate the invention further, the process was applied to the final, deionized greens from an enzyme-enzyme hydrolysate.

The composition of the greens, based on an average of several samples, was as follows:

Table 2

| | Greens Composition |
|---|---|
| Sugar | % of component sugar as a % of total sugar present |
| dextrose | 58.7 |
| maltose | 16.2 |
| isomaltose | 12.5 |
| trisaccharide | 2.9 |
| DP4 | 1.2 |
| DP5 and higher polysaccharides | 8.7 |

The glucose isomerase utilized was derived from a strain of *Streptomyces olivochromogenes*.

The transglucosidase was obtained by clay absorption in the following manner. An *Aspergillus niger* culture filtrate was mixed with Florex clay at pH 3.5-4.0, to effect absorption of the transglucosidase. The clay was then filtered out and washed with acetate buffer at pH 3.5, then eluted with phosphate buffer at pH 7.0. The transglucosidase was then precipitated onto a Dicalite (diatomaceous earth) carrier with 2-propanol, followed by air drying. Each gram of the thus purified enzyme preparation contained the activity from about 25 ml. of the culture broth.

The activity of the adsorbed transglucosidase was assayed in the following manner. Twenty-five mg. of the adsorbed enzyme was incubated in 2 ml. of 0.05 M acetate buffer (pH 4.5) with nitrogen sparging, at an isomaltose concentration of 0.01 M at 37°C for 10 minutes. The amount of dextrose was then determined. One unit of enzyme is defined as the amount that produces 1 m$\mu$ mole of dextrose under the assay conditions. The activity of the Dicalite-enzyme preparation was 120,000 units/g.

For comparative purposes, reconversion of greens was also conducted with a culture filtrate of *Paecilomyces varioti* having an isomaltase activity of 5,000 units/ml., which is approximately equivalent to the activity of the Dicalite-enzyme complex (4,800 units/ml.). Both exhibited the same mode of action on greens.

The greens, at 50% solids d.s., were subjected first to isomerization, by treatment with 400 units/g of the isomerase per gram of substrate dry substance, at an initial pH 6.2 as established by 0.05M phosphate buffer, at 70°C, in the presence of 0.01 M MgSO$_4$, for two days. The isomerizate analysed 38% dextrose and 20% ketose, based on total solids present.

The isomerizate was divided in two portions. One portion was reconverted with the Dicalite-enzyme complex, and the other with the transglucosidase from the *P. varioti*. The results were essentially the same in each case. The reconversion was effected by treatment of the isomerisate with 25,000 units of the transglucosidase enzyme preparation per gram of substrate, d.s., at 60°C for 2 days. The amount of dextrose was increased to 58%, while the ketose component decreased from 20% to 19%. The total increase in dextrose and levulose was 17% as compared to the initial greens, i.e., there was a net increase of 2% in the dextrose concentration, and the creation of ketose values of 14%, all based on total solids.

EXAMPLE 3

Isomerization, Dilution, and Reconversion of Second Greens; Effects of Process Parameters The same initial greens supply was used as in Example 2, at 50% dry solids.

The greens supply was incubated with 400 units of isomerase per gram of substrate d.s. at pH 6.2 and 70°C for 2 days. The isomerizate was then diluted to 30% d.s., divided into several portions, and then each of three portions was reconverted with 25,000 units of transglucosidase per gram of substrate d.s., at pH 4.5 for 4 days, at temperatures of 37°C., 50°C, and 60°C, for each of the three different portions, respectively.

The batch that was reconverted at 37°C had a final analysis of approximately 30% levulose and 52% dextrose: The batch reconverted at 50°C analyzed at approximately 30% levulose and 58% dextrose; and the batch reconverted at 60°C analyzed at approximately 30% levulose and 60% dextrose; all of the foregoing percentages being based on total dry substance.

These data demonstrate that the optimum temperature for reconversion is approximately 60°C.

Using similar techniques, the effect of different transglucosidase dosages on the isomerizate was observed. Three portions of the diluted isomerizate mentioned above were reconverted by treatment with transglucosidase at 5,000 units/g, 10,000 units/g, and 25,000 units/g, based on substrate dry substance, respectively, at pH 4.5 and at 60°C. After four days of treatment, the products had the following respective contents of dextrose, approximately: 55%, 59%, and 62%, d.s., respectively, and each had a levulose content of about 30%, d.s. The dosage level of 25,000 units/g appeared to be desirable for obtaining the maximum yield of dextrose.

A study of the effect of different levels of glucose isomerase dosage on greens indicated that an enzyme dosage of about 400 units/g of substrate d.s. is necessary for maximum ketose yield.

Greens isomerized under optimum conditions and then reconverted at 30% concentration had the following composition:

Table 3

| Sugar | Product Composition % of component sugar as a % of total sugar present |
|---|---|
| dextrose | 59.7 |
| ketose | 24.6 |
| isomaltose | 6.6 |
| DP3 | 1.9 |
| Other | 7.1 |

CONCLUSION

The process of the invention takes advantage of the equilibrium conditions that exist between dextrose, isomaltose, and maltose, and dextrose and levulose.

Generally, as has been demonstrated, the process of the invention consists of two sequential steps, i.e., isomerization followed by conversion with transglucosidase. The isomerization transforms up to about 50% of the initial dextrose to levulose, thus reducing the dextrose content so as to favor dextrose formation during the treatment with transglucosidase. In this way, the total monosaccharide content of the end product is maximized.

The process of the invention can be practised in several ways.

One preferred technique is a continuous process in which hydrol, such as second greens, is passed first through a column packed with a source of xylose isomerase, then through a column containing bentonite on which transglucosidase had been absorbed.

The transglucosidase need not be derived by clay absorption from amylase, however, instead, it may be derived directly from a microorganism. Thus, isomaltase derived from *Paecilomyces varioti* and from *Penicillium brefeldianum* has been utilized successfully, over a wide range of greens concentrations. The enzyme treatment with such enzymes has been carried out successfully in 0.05 M succinate NaOH buffer at pH 4.0 at 60°C for 2 days. Purified enzymes generally produce higher conversion rates than crude enzymes. One way to produce purified enzyme is by treatment of the culture broth of the source microoogranism with an adsorbing clay, preferably an activated clay.

Simultaneous enzymatic isomerization and transglucosidase conversion has been found to be ineffective. The enzymes apparently are incompatible to some extent, and very little ketose is formed. When practising batch isomerization in the process of this invention, the isomerase is largely exhausted at the conclusion of the isomerization, so that it has little or no effect on the subsequent treatment with isomaltase.

No significant difference is observed when the process of the invention is practised with acid-enzyme greens rather than enzyme-enzyme greens. However, the compositions of saccharides in enzyme-enzyme and acid-enzyme greens, before and after treatment, is somewhat different.

The equilibrium points in the reversion of dextrose and conversion of maltose were investigated, using enzyme-enzyme greens. During the transglucosidase treatment, the equilibrium points at greens concentrations of 10%, 30%, and 50%, d.s., respectively, appeared to be at about 95%, 85%, and 75%, d.s. in terms of dextrose content.

What is claimed is:

1. A process for increasing the sweetness and monosaccharide content of a starch hydrolysate, comprising:
   a. subjecting a starch hydrolysate containing dextrose, maltose, isomaltose and oligosaccharides to enzymatic isomerization to isomerize at least a portion of the dextrose in said starch hydrolysate to levulose, and then
   b. treating said hydrolysate with an enzyme preparation having isomaltase or transglucosidase activity to produce a syrup which is sweeter and contains a higher amount of monosaccharides than said starch hydrolysate.

2. The process in accordance with claim 1, wherein the concentration of solids in the starch hydrolysate does not exceed about 50%, by weight, dry substance.

3. The process in accordance with claim 1, wherein the concentration of solids in the initial starch hydrolysate is about 50%, by weight, dry substance, including as a preliminary step:
   subjecting the starch hydrolysate to the action of an enzyme preparation having a isomaltase or transglucosidase activity.

4. The process of claim 1, wherein the enzyme preparation is employed at a dosage level of about 25,000 units/g d.s. in the substrate.

5. The process of claim 1, wherein said enzyme preparation is derived from *Aspergillus niger*.

6. The process of claim 1, wherein the enzyme preparation is derived from *Paecilomyces varioti* or *Penicillium brefeldianum*.

7. A process for the enzymatic conversion of a dextrose mother liquor, comprising:
   a. subjecting a dextrose mother liquor containing dextrose, maltose, isomaltose and oligosaccharides having a solids concentration that does not exceed 50%, by weight, dry substance to the action of xylose isomerase, and then
   b. subjecting the isomerizate to the action of an enzyme preparation having isomaltase or transglucosidase activity.

8. The process in accordance with claim 7, wherein the enzyme preparation is absorbed on clay.

9. The process in accordance with claim 7, wherein the concentration of solids in the initial dextrose mother liquor is about 50%, by weight, dry substance, including a preliminary step:
   subjecting the mother liquor to the action of an enzyme preparation having isomaltase or transglucosidase activity absorbed on clay.

10. A process in accordance with claim 7, including the step of diluting the isomerizate prior to treatment with the enzyme preparation.

11. The process of claim 7, wherein said enzyme preparation is derived from *Aspergillus niger*.

12. A continuous process for increasing the sweetness and monosaccharide content of a dextrose mother liquor, comprising:
   a. continuously passing a dextrose mother liquor containing dextrose, maltose, isomaltose and oligosaccharides through a column packed with a xylose isomerase enzyme preparation, and then
   b. continuously passing said liquod liquor a column containing an enzyme preparation having isomaltase or transglucosidase activity and said preparation being absorbed on bentonite.

13. The process of claim 12, wherein said enzyme preparation is derived from *Aspergillus niger*.

14. A process for increasing the monosaccharide content of a levulose-bearing syrup comprising:
   subjecting an enzymatically isomerized starch hydrolysate, containing dextrose, levulose, disaccharides and oligosaccharides which has been produced by enzymatically isomerizing a starch hydrolysate to convert at least a portion of the dextrose in said starch hydrolysate to levulose, to the action of a transglucosidase enzyme preparation to obtain a levulose-bearing syrup having a higher monosaccharide content than said enzymatically isomerized starch hydrolysate.

15. The process of claim 14, wherein said enzyme preparation is derived from *Aspergillus niger*.

16. A continuouse process for increasing the sweetness and monosaccharide content of a hydrol liquor, comprising:
   a. acid or enzyme thinning a starch slurry to a D.E. of 10 or less, followed by enzymatic saccharification of the thinned starch to obtain a hydrolysate having a D.E. above about 95,
   b. crystallizing the dextrose from said hydrolysate to obtain a crystalline dextrose and a hydrol,
   c. continuously passing said hydrol through a column packed with a xylose isomerase enzyme preparation to partially isomerize the dextrose in said hydrol and thereafter
   d. continuously passing said hydrol containing partially isomerized dextrose through a column containing an enzyme preparation having isomaltase or transglucosidase activity, said enzyme preparation having been absorbed on bentonite.

17. The process of claim 12, wherein said enzyme preparation is derived from *Aspergillus niger*.

* * * * *